US012569128B2

(12) United States Patent
Commuri et al.

(10) Patent No.: US 12,569,128 B2
(45) Date of Patent: Mar. 10, 2026

(54) APPARATUS AND METHOD FOR DETECTING CERVICAL CANCER

(71) Applicant: BOARD OF REGENTS OF THE NEVADA SYSTEM OF HIGHER EDUCATION, on behalf of THE UNIVERSITY OF NEVADA, RENO, Reno, NV (US)

(72) Inventors: Sesh Commuri, Reno, NV (US); Garrett Winkelmaier, Reno, NV (US); Paloma Cepeda Andrade, Sparks, NV (US)

(73) Assignee: Board of Regents of Nevada System of Higher Education on behalf of the University of Nevada, Reno, Reno, NV (US)

( * ) Notice: Subject to any disclaimer, the term of this patent is extended or adjusted under 35 U.S.C. 154(b) by 336 days.

(21) Appl. No.: 18/037,114

(22) PCT Filed: Dec. 3, 2021

(86) PCT No.: PCT/US2021/061870
§ 371 (c)(1),
(2) Date: May 16, 2023

(87) PCT Pub. No.: WO2022/120212
PCT Pub. Date: Jun. 9, 2022

(65) Prior Publication Data
US 2024/0065540 A1 Feb. 29, 2024

Related U.S. Application Data

(60) Provisional application No. 63/121,432, filed on Dec. 4, 2020.

(51) Int. Cl.
*A61B 1/303* (2006.01)
*A61B 1/00* (2006.01)
(Continued)

(52) U.S. Cl.
CPC ........ *A61B 1/303* (2013.01); *A61B 1/000095* (2022.02); *A61B 1/00016* (2013.01);
(Continued)

(58) Field of Classification Search
CPC ............... A61B 1/303; A61B 2576/00; A61B 1/000095; G06T 7/0016;
(Continued)

(56) References Cited

U.S. PATENT DOCUMENTS 6,101,408 A * 8/2000 Craine ................. A61B 5/0086
382/128
6,896,653 B1 * 5/2005 Vail, III ............... A61B 1/0638
600/109
(Continued)

FOREIGN PATENT DOCUMENTS

| WO | 2019/030749 A1 | 2/2019 |
| WO | 2019/070998 A1 | 4/2019 |
| WO | 2020/076644 A2 | 4/2020 |

OTHER PUBLICATIONS

International Search Report and Written Opinion dated Mar. 14, 2022 which was issued in connection with International Application No. PCT/US2021/061870, 8 pages.

*Primary Examiner* — Anh Tuan T Nguyen
*Assistant Examiner* — Jae Woo

(57) ABSTRACT

A method for automatic, image-based detection of abnormalities in a patient's cervix is disclosed. In an embodiment, a Cervitude Imaging System (CIS) processor of a CIS device illuminates a light source affixed to a distal end of a probe housing, receives cervical image data of the patient from a camera affixed to the distal end of the probe housing, generates a reconstructed image that includes reduced specular reflections, and segments the reconstructed image into at least one region of interest (ROI). The process also includes the CIS processor transmitting the reconstructed (Continued)

image comprising the at least one ROI to at least one of a host system and an input/output device.

16 Claims, 4 Drawing Sheets

(51) Int. Cl.
| | | |
|---|---|---|
| *A61B 1/05* | (2006.01) | |
| *A61B 1/06* | (2006.01) | |
| *G06T 7/00* | (2017.01) | |
| *G06T 7/11* | (2017.01) | |

(52) U.S. Cl.
CPC .............. *A61B 1/0002* (2013.01); *A61B 1/05* (2013.01); *A61B 1/0638* (2013.01); *A61B 1/0676* (2013.01); *A61B 1/0684* (2013.01); *G06T 7/0016* (2013.01); *G06T 7/11* (2017.01); *G06T 2207/10024* (2013.01); *G06T 2207/30096* (2013.01)

(58) Field of Classification Search
CPC ......... G06T 2207/10024; G06T 7/0012; G06T 7/11; G06T 2207/30096
See application file for complete search history.

(56) References Cited

U.S. PATENT DOCUMENTS

| | | | | |
|---|---|---|---|---|
| 2005/0215858 | A1* | 9/2005 | Vail, III | A61B 1/303 |
| | | | | 600/109 |
| 2007/0055128 | A1 | 3/2007 | Glossop | |
| 2009/0062662 | A1* | 3/2009 | Zuluaga | A61B 5/742 |
| | | | | 600/478 |
| 2011/0313297 | A1* | 12/2011 | Ishihara | A61B 1/043 |
| | | | | 600/476 |
| 2012/0292530 | A1* | 11/2012 | Ono | A61B 5/0084 |
| | | | | 250/458.1 |
| 2015/0276602 | A1* | 10/2015 | Ishihara | A61B 1/000094 |
| | | | | 250/216 |
| 2015/0320319 | A1* | 11/2015 | Alfano | A61B 1/00142 |
| | | | | 600/425 |
| 2016/0073853 | A1* | 3/2016 | Venkatesan | H04N 7/183 |
| | | | | 348/68 |
| 2017/0105613 | A1* | 4/2017 | Tsuruta | A61B 1/0625 |
| 2017/0319147 | A1* | 11/2017 | Wang | A61B 1/043 |
| 2018/0116581 | A1* | 5/2018 | Prasad | G06T 7/0012 |
| 2018/0357793 | A1* | 12/2018 | Boes | G01J 3/10 |
| 2019/0166312 | A1* | 5/2019 | Tashayyod | H04N 23/951 |
| 2019/0204068 | A1* | 7/2019 | Sonoda | A61B 1/00009 |
| 2019/0387965 | A1* | 12/2019 | Utsunomiya | A61B 1/000095 |
| 2020/0041261 | A1* | 2/2020 | Bernstein | A61B 90/37 |
| 2020/0043613 | A1* | 2/2020 | Zhang | G16H 40/63 |
| 2020/0258224 | A1* | 8/2020 | Endo | A61B 1/0005 |
| 2020/0305698 | A1* | 10/2020 | Oosake | A61B 1/000096 |
| 2020/0315444 | A1* | 10/2020 | Ramanujam | A61B 1/307 |
| 2021/0012886 | A1* | 1/2021 | Kubota | G06T 7/0012 |
| 2021/0227133 | A1* | 7/2021 | Mizoguchi | A61B 1/042 |
| 2021/0361142 | A1* | 11/2021 | Kitamura | A61B 5/7267 |
| 2021/0374953 | A1* | 12/2021 | Asiedu | A61B 1/000094 |
| 2022/0296090 | A1* | 9/2022 | Ouyang | A61B 1/00103 |
| 2022/0346632 | A1* | 11/2022 | Tanaka | A61B 1/000095 |
| 2023/0030057 | A1* | 2/2023 | Aoyama | A61B 1/06 |
| 2023/0052100 | A1* | 2/2023 | Devani | G06T 7/62 |

* cited by examiner 300
302
304
306
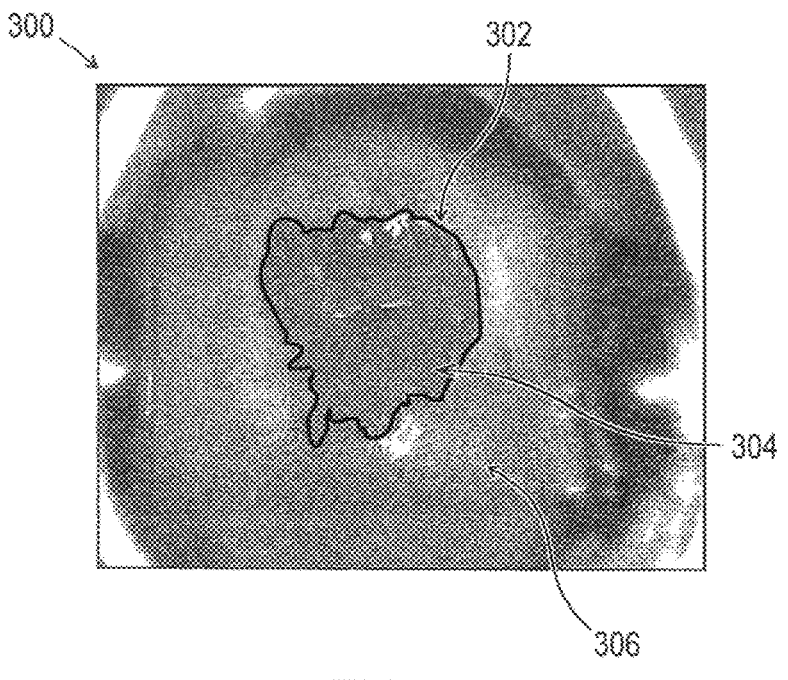
FIG. 3A
310
312
314
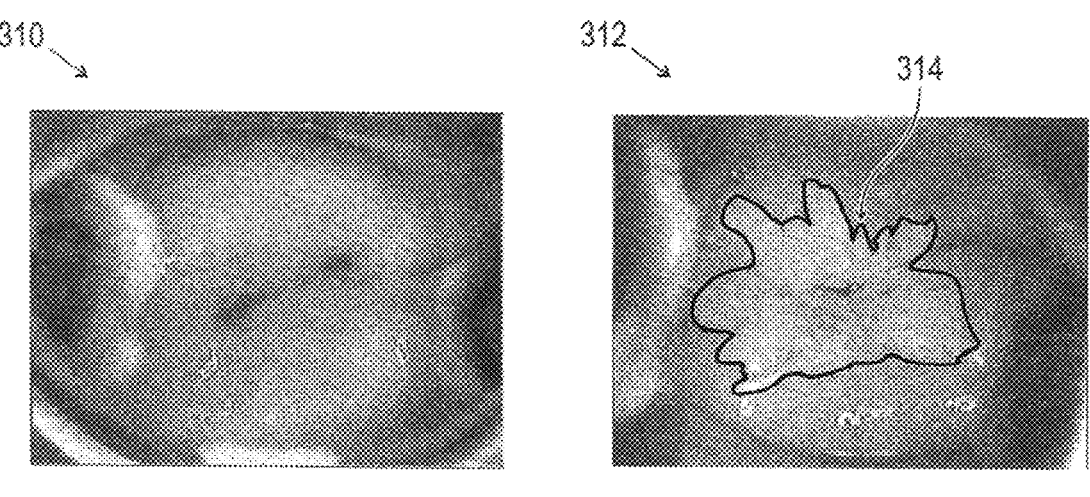
FIG. 3B                    FIG. 3C

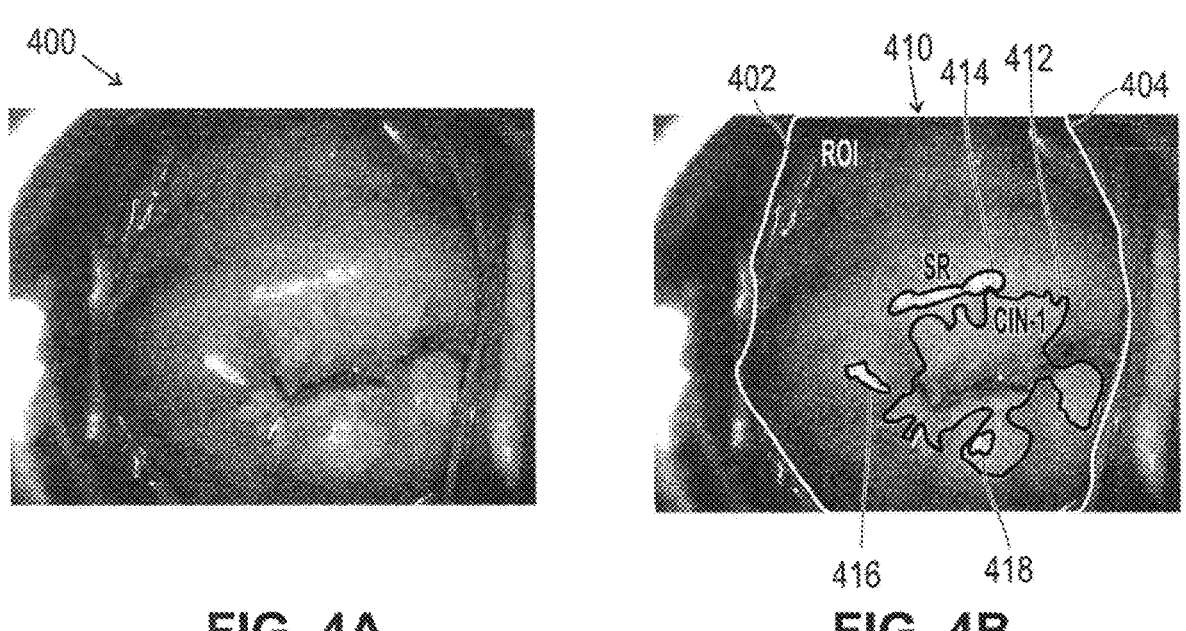
FIG. 4A            FIG. 4B
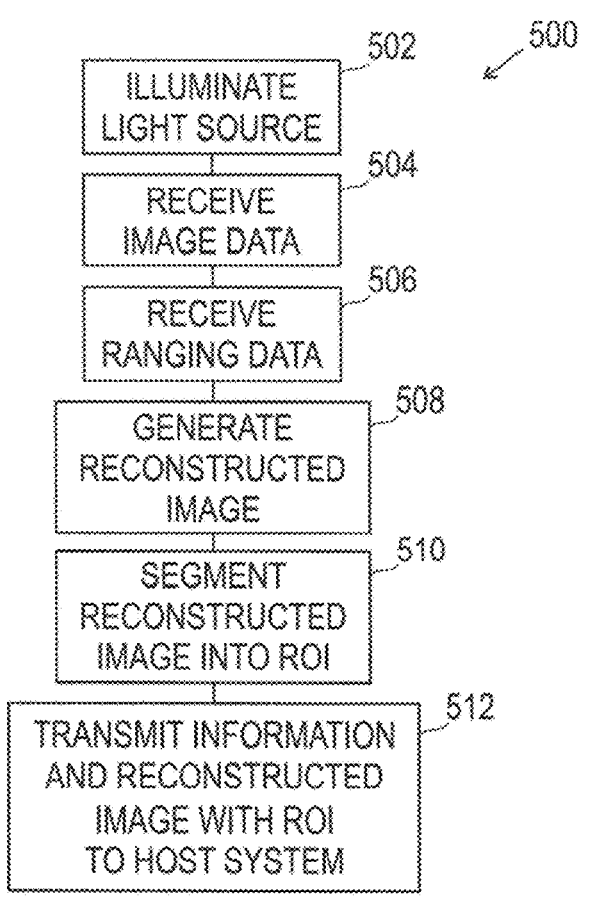
FIG. 5

APPARATUS AND METHOD FOR DETECTING CERVICAL CANCER

CROSS REFERENCE TO RELATED APPLICATION

This application claims the benefit of U.S. Provisional Patent Application No. 63/121,432 filed on Dec. 4, 2020, and International Application No. PCT/US21/61870 which was filed on Dec. 3, 2021, the contents of which provisional application are hereby incorporated by reference for all purposes.

FIELD OF THE INVENTION

The invention generally relates to a Cervitude Imaging System (CIS) for capturing an image of the human cervix that is used for detecting the presence, location and extent of one or more precancerous lesions on the cervix. More specifically, in some embodiments the CIS is a low-cost, portable device that can be used in conjunction with a computer to detect and analyze precancerous lesions on the human cervix, for example, during a routine pelvic exam at the point of care (POC). In some implementations, the CIS can be utilized to detect and analyze the precancerous lesions at a POC location in resource-constrained and/or middle-to-low income countries.

BACKGROUND

Cervical cancer is the fourth most frequent cancer in women worldwide representing 6.6% of all cancers affecting women. Most cervical cancer cases are caused by various strains of the human papillomavirus (HPV). According to the World Health Organization, mortality rates related to cervical cancer are higher in low-to-middle income countries primarily due to lack of resources. Annually, over 90% of all instances of cervical cancer are found in low-to-middle income countries. Once detected and diagnosed, cervical cancer is one of the most treatable cancers. However, more than 55% of the cases in the low-to-middle income countries (approximately 266,000 out of 475,500 cases) end up being fatal. Contributing factors to this high rate of death include lack of awareness and access to care, poor staining technique during colposcopy, poor magnification and resolution of the current devices on the market, cumbersome handling of colposcopes due to size and need for electrical power source, and multi-visit, unpleasant, time-consuming patient experiences.

Typical screening methods for detecting cervical cancer currently include highly invasive techniques such as the Papanicolaou test (PAP smears or PAP test), HPV testing, colposcopies, cytology screenings, biopsies, detection of lesions with the naked eye, and genetic testing (genetic bioagent detectors). A colposcope is a large microscope-like device that is used to illuminate and examine a magnified view of the cervix as well as the vagina and vulva. If abnormal smears are observed, a biopsy of the affected area of the cervix is performed.

There are more than one hundred (100) strains of Human Papilloma (Wart) Virus (HPV) of which thirteen (13) types are responsible for cervical cancer. HPV-16 and HPV-18 strains are the most common. HPV infection usually subsides by itself, but if persistent a patient might have to get PAP smears frequently. An abnormal PAP smear may show atypical cells which could be due to an abnormality, infection, or reaction to inflammation. Most abnormalities of the ectocervix are stratified squamous cell abnormalities. The abnormality usually manifests in the transformation zone (squamo-columnar junction). Abnormal looking cells are referred to as "favoring dysplasia" or of "unknown significance". If dysplasia is determined, the subject is referred to a colposcopist. Occasionally, Atypical Glandular cells of Unknown Significance (AGUS), Adeno Carcinoma In-Situ of the cervix (ACIS), or endometrial cells are also observed.

TABLE 1

| Changes in the Cervix | | | | | | |
| --- | --- | --- | --- | --- | --- | --- |
| Normal | HPV | CIN-1 | CIN-2 | CIN-3 | CIN-3 (GE) | Cancer |

Table 1 above characterizes the changes in the cervix from normal to cancerous. The presentations from CIN-1-CIN-3 (Glandular Extensions—GE) are precancerous and are curable. Low grade changes in the cervix are termed "mild dysplasia" and referred to as CIN-1. High grade changes are termed as "severe dysplasia" and could be CIN-2, CIN-3 or CIN-3 with Glandular Extensions (GE). In an extreme case a high grade change could be Carcinoma In-Situ (CIS) or cancer. Cervical cancer is treatable if detected and diagnosed early. In particular, cryotherapy or loop electrosurgical excision procedure (LEEP) can provide effective and appropriate treatment for the majority of women who screen positive for precancerous lesions, and both "screen-and-treat" and "screen, diagnose and treat" are valuable approaches.

The main equipment on the market used in detecting cervical cancer through imaging is the colposcope and the speculum. The speculum opens the vaginal walls so the colposcope can obtain an image of the cervix through the opening of the speculum. These two pieces of equipment dominate the current market for cervical cancer detection. In an example of a conventional cervix examination, a patient is first made to lie down on her back with her feet in stirrups. The doctor then uses a speculum to keep the vagina open and to expose the cervix. The surface of the cervix is rinsed with saline water and then treated with a vinegar solution. The doctor then uses a colposcope to illuminate and visually study an enlarged image of the cervix. Although this testing procedure is nearly pain-free, it can be uncomfortable for the patient and difficult for the doctor to perform. Specifically, it can be difficult to quantify different characteristics of any lesions that are found unless the patient is examined by a trained professional. Even then, diagnosis can be highly subjective and may lead to a misdiagnosis or in some cases an unnecessary biopsy.

Moreover, colposcopes are expensive machines for a doctor's office to purchase as such devices may cost upwards of ten thousand to fifteen thousand U.S. dollars ($10,000-$15,000). In addition, the examination cost for the patient can also be fairly high. For example, the examination cost for a patient with insurance is typically about one thousand dollars ($1,000) and may be upwards of twenty-five hundred dollars ($2,500) for patients without insurance. Due to the high equipment and procedure costs, and the need for trained colposcopists, colposcopy examinations are not regularly conducted in low-income areas. Consequently, there are higher rates of undiagnosed cervical cancer in lower socio-economic areas (or poorer populations) resulting in higher mortality rates for women from cervical cancer.

Duke University announced development of a "pocket colposcope" in 2017 that is less expensive than a clinical colposcope. The pocket colposcope is small, portable, and can be used to self-screen at home but has yet to be fully validated. In addition, the pocket colposcope includes only white light illumination and thus cannot be used to study vasculature using green light or tumors using Fluorescent Sodium stains. Furthermore, the pocket colposcope has no integrated viewing system and does not include any algorithms that can detect and/or highlight pre-cancerous lesions on the cervix.

Therefore, a need exists for low-cost and easily accessible tool that can be used for screening and for the early detection of abnormal changes in the cervix that may later turn into invasive cancer. Such a low-cost tool would be especially beneficial for use in low-to-middle income countries and/or neighborhoods.

SUMMARY OF THE INVENTION

Presented are methods and low-cost devices for use in screening for early detection of abnormal changes in a patient's cervix. In some embodiments, a method for automatic, image-based detection of abnormalities in the patient's cervix includes a Cervitude Imaging System (CIS) processor of a CIS device illuminating a light source affixed to a distal end of a probe housing of the CIS device, receiving cervical image data of the patient from a camera affixed to the distal end of the probe housing and generating a reconstructed image that includes reduced specular reflections. The process also includes the CIS processor segmenting the reconstructed image into at least one region of interest (ROI) and transmitting the reconstructed image including the at least one ROI to at least one of a host system and an input/output device.

In some embodiments wherein the reconstructed image including the at least one ROI is transmitted to a host system, the host system is operably connected to a database configured for storing data and instructions, and in some implementations the host system compares the reconstructed image comprising the at least one ROI with previous image data of the patient to determine any changes in the cervix of the patient.

In some embodiments, the method also includes the CIS processor receiving ranging data from a ranging sensor affixed to the distal end of the probe housing and generating, based on the ranging data, location and size data of a lesion on the cervix of the patient in the ROI. In addition, the CIS processor may transmit the location and size data to at least one of a host system and an input/output device.

In some embodiments, generating the reconstructed image comprises the CIS processor generating a brightness map using the received image data, discarding areas of the brightness map where specular reflection is predominant, and averaging red, blue and green (RGB) values from the image data to form the reconstructed image. In some implementations of the process, after segmenting the reconstructed image into at least one ROI, the CIS processor compares the at least one ROI to known abnormal tissue type data stored in a storage device, identifies based on the comparison, a lesion type, and transmits an indication of the lesion type to at least one of a host system and an input/output device. In addition, the indication of the lesion type may include one of normal tissue, pre-cancerous tissue or cancerous tissue. In some implementations, after illuminating the light source, the CIS processor receives image data from the camera associated with a plurality of cervical images of the patient, generates a brightness map for each of the plurality of cervical images, discards areas of the brightness map for each of the plurality of cervical images where specular reflection is predominant, generates preprocessed image data for each cervical image by averaging red, blue and green (RGB) values from the image data and segments the preprocessed image data for each cervical image into at least one region of interest (ROI), and in some embodiments transmits the segmented preprocessed image data for each cervical image to at least one of a host system and an input/output device.

In another aspect, disclosed is a portable Cervitude Imaging System (CIS) device for capturing cervical images of a patient. In an embodiment, the CIS device includes a probe housing comprising a camera and a light source and a control housing connected to the probe housing, the control housing comprising a CIS processor, a communication device, a power supply and a storage device. In some embodiments, the storage device stores processor executable instructions which when executed causes the CIS processor to illuminate the light source, receive from the camera cervical image data of the patient, generate a reconstructed image comprising reduced specular reflections and segment the reconstructed image into at least one region of interest (ROI). In some embodiments, the storage device also includes instructions which when executed cause the CIS processor to transmit the reconstructed image including the at least one ROI to a host system.

In some embodiments, the CIS device also includes at least one of a ranging sensor housed in the probe housing and operably connected to the CIS processor, the ranging sensor operable to provide location data to the CIS processor, and an input/output device operably connected to the CIS processor. In some implementations, the storage device further comprises instructions which when executed cause the CIS processor to generate location data and size data of any lesions in the ROI based on the location data, and to transmit the location data and size data of any lesions to at least one of a host system and the input/output device.

In embodiments disclosed herein, the light source of the CIS device includes a plurality of light emitting diodes (LEDs). In some implementations, the plurality of LEDs includes at least one white LED, one blue LED, and one green LED. In addition, the CIS device may include an electronic circuit operably connected between the CIS processor and the camera, the light source and the ranging sensor, and in some implementations the electronic circuit converts output signals from at least one of the camera and the ranging sensor into digital signals for input to the CIS processor.

In some further implementations, the instructions for generating the reconstructed image further include instructions which when executed cause the CIS processor to generate a brightness map using the received image data, discard areas of the brightness map where specular reflection is predominant, and average red, blue and green (RGB) values from the image data to form the reconstructed image. In addition, the storage device may further include, subsequent to the instructions for segmenting the reconstructed image into at least one ROI, instructions which when executed cause the CIS processor to compare the at least one ROI to known abnormal tissue type data stored in the storage device, identify, based on the comparison, a lesion type, and transmit an indication of the lesion type to at least one of a host system and an input/output device. The indication of the lesion type may include one of normal tissue, pre-cancerous tissue or cancerous tissue.

In some further embodiments, the storage device stores further instructions, subsequent to the instructions for illuminating the light source, that causes the CIS processor to receive image data from the camera associated with a plurality of cervical images of the patient, generate a brightness map for each of the plurality of cervical images, discard areas of the brightness map for each of the cervical images where specular reflection is predominant, generate preprocessed image data for each cervical image by averaging red, blue and green (RGB) values from the image data, segment the preprocessed image data for each cervical image into at least one region of interest (ROI) and transmit the segmented preprocessed image data for each cervical image to at least one of a host system and an input/output device. In addition, the storage device may store at least one of current image data of the patient, previous image data of the patient, and any prior diagnostic data of the patient. In some embodiments the host system may also be operably connected to a database, and at least one of current image data of the patient, previous image data of the patient, and any prior diagnostic data of the patient may be stored in the database.

BRIEF DESCRIPTION OF THE DRAWINGS

Features and advantages of some embodiments of the present disclosure, and the manner in which the same are accomplished, will become more readily apparent upon consideration of the following detailed description taken in conjunction with the accompanying drawings, which illustrate preferred and example embodiments and which are not necessarily drawn to scale, wherein:

FIG. 3A is an example image of a healthy cervix;

FIGS. 3B and 3C depict a first image of the cervix of a patient before application of acetic acid and a second image of the cervix after application of acetic acid, respectively, to illustrate how using acetic acid can highlight potential precancerous lesions;

FIG. 4A depicts an original image of the cervix of a patient which contains several areas of interest in accordance with the disclosure;

FIG. 4B is an image of the cervix of FIG. 4A depicting a manual segmentation between boundary lines of a cervical region of interest (ROI) that contains areas recognized as specular reflection (SR) areas, and wherein area an area can be diagnosed as being an acetowhite staining (CIN-1) area interpreted as being a pre-cancerous lesion in accordance with embodiments of the disclosure; and FIG. 5 is a flowchart illustrating a CIS device process according to embodiments of the disclosure.

DETAILED DESCRIPTION

In general, and for the purposes of introducing concepts of disclosed embodiments, disclosed are a portable Cervitude Imaging System (CIS) device, system and methods for the early detection of abnormalities in the cervix, and specifically cervix tissue suspected of being physiologically changed as a result of pre-cancerous and/or cancerous activity. In embodiments disclosed herein, the CIS device is a portable, handheld device designed for insertion into the vaginal opening to examine the cervix, and includes components for capturing images, for processing the images, for providing ranging information and for communicating with a host computer system. In addition, in some implementations an extracorporeal CIS device is disclosed, wherein the extracorporeal CIS device is utilized outside the body of a patient in conjunction with a speculum. Such an extracorporeal CIS device can augment a conventional pelvic examination procedure by capturing precision images which cannot be discerned with the naked eye of an observer. Accordingly, implementations of the CIS device include image acquisition and data processing capabilities that may be utilized to present images and/or provide information to a doctor and/or other medical personnel useful for locating and/or detecting and/or characterizing precancerous lesions and cancerous tissue in the cervix of a patient.

Figure 1A:
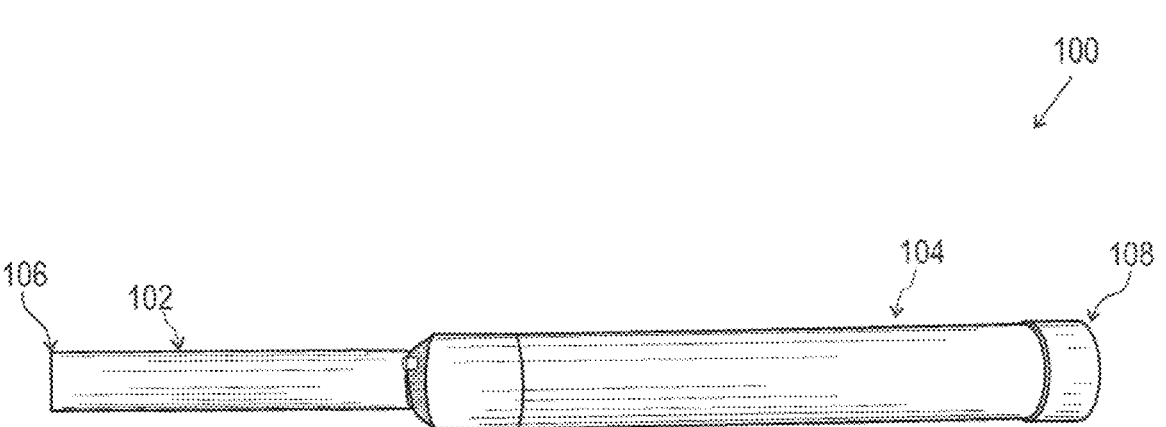
FIG. 1A is a side view of a Cervitude imaging system (CIS) device according to some embodiments of the disclosure.

FIG. 1A depicts an embodiment of a CIS device 100 (or CIS capture probe) according to some embodiments. The CIS device 100 of FIG. 1A includes a generally cylindrical probe housing 102 connected to a generally cylindrical control housing 104. The probe housing 102 houses an imaging system having components at a first distal end 106 (shown in FIG. 1B) and is designed to have a diameter and a length suitable for insertion through the vagina or through a speculum to observe the cervix of the patient. The probe housing 102 may be made of a plastic, metal or composite material that can be sanitized, and in some implementations may be equipped with a disposable sleeve.

Referring again to FIG. 1A, the control housing 104 houses control circuitry (not shown) operable to control the functions of the imaging system as disclosed herein (discussed below with reference to FIG. 2). An ON/OFF switch (not shown) may be located at a second distal end 108 and be operable to turn power ON from an electrical power supply (see FIG. 2) housed within the control housing 104 to power the imaging system 106 when the CIS device is being used, and to turn power OFF when finished. The control housing 104 may be constructed of the same or a different material as the probe housing 102 and may have a diameter the same as the diameter of the probe housing 104, or larger as depicted. In some embodiments, the control housing 104 is sized and/or dimensioned to be easily gripped by the human hand.

Figure 1B:
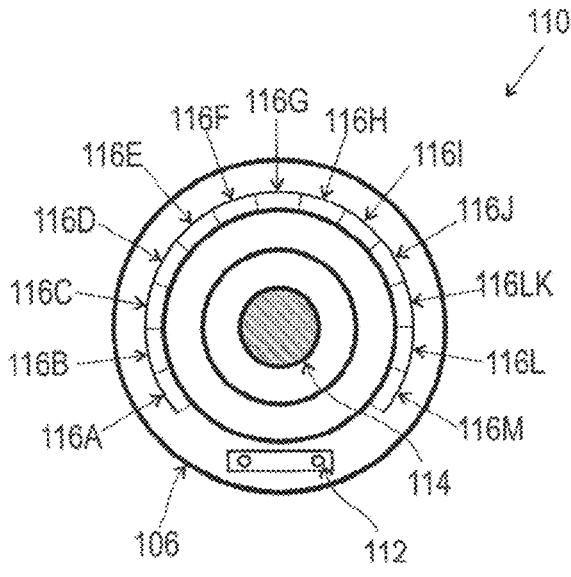
FIG. 1B is an enlarged front view of the distal end of the CIS device of FIG. 1A illustrating components of an imaging and ranging system in accordance with some embodiments of the disclosure.

FIG. 1B is an enlarged front view of the distal end 106 of the CIS device 100 of FIG. 1A illustrating components of an imaging and ranging system 110 according to some embodiments. The components of the imaging and ranging system 110 include a range sensor 112 (such as an ultrasonic sensor), a camera lens 114 (or imaging sensor) of a camera, and a light source including a plurality of light-emitting diodes (LEDs) 116A to 116M. The LEDs 116A to 116M may be turned ON to illuminate the cervix of a patient when the CIS device 100 (or handheld probe) is in use, and turned OFF when the CIS device is not in use. As mentioned earlier, the probe housing 102 is shaped and sized so that it can be used independently or with a speculum (not shown) to examine the cervix. In addition, each of the LEDs 116A to 116M may be separately controllable by a processor (shown in FIG. 2) during operation as explained below and may differ in color output and/or intensity. For example, LEDs 116A, 116D, 116G, 116J and 116M may be ultra-bright white light LEDs, while LEDs 116B, 116E, 116H and 116K may be blue light LEDs, and LEDs 116C, 116F, 116I and 116L may be greenlight LEDs. Also, more or fewer LEDs may be utilized in some embodiments.

Figure 2:
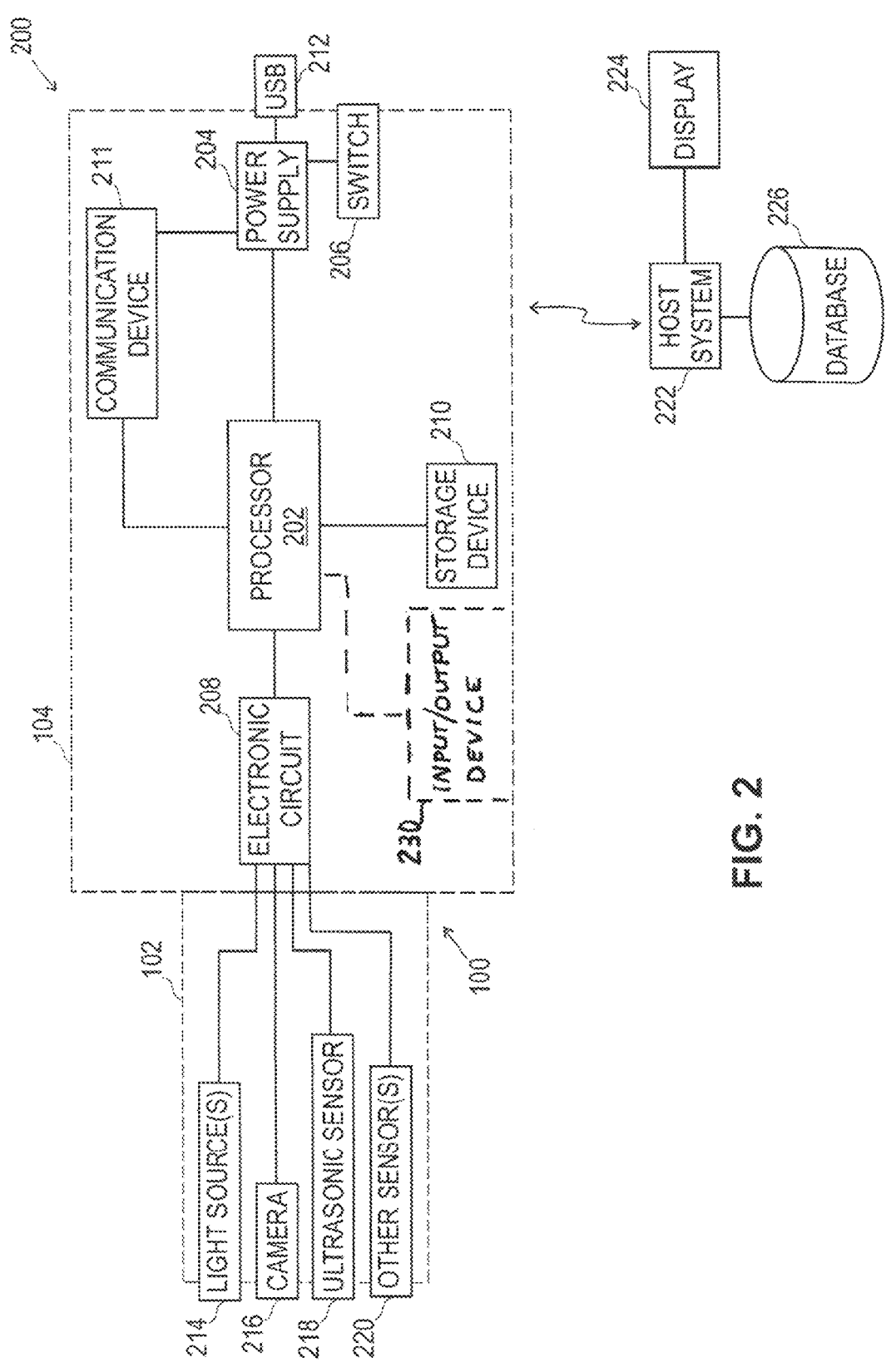
FIG. 2 is a block diagram of a cervical imaging system including the CIS device in accordance with some embodiments of the disclosure.

FIG. 2 is a block diagram of a cervical imaging system 200 in accordance with some embodiments. In an implementation, as mentioned earlier the CIS device 100 includes a probe housing 102 connected to a control housing 104. As shown in FIG. 2, in some embodiments the control housing 104 houses a CIS processor 202 (which may include one or more microprocessors) that is operably connected to a rechargeable and/or integrated power supply 204, wherein the power supply is operably connected to a switch 206 and to an USB port 212. The switch 206 may be sized and/or dimensioned for use by a person, such as a doctor or medical technician, to turn power ON and OFF to the CIS device 100. The USB port 212 may be used for connection to a power source to recharge the power supply 204 and/or the CIS device 100 may be configured for charging through a wireless charging station. As shown, the CIS processor 202 is also operably connected to an electronic circuit 208 (which may be, for example, an analog-to-digital converter circuit), a storage device 210 and communications device 211.

Referring again to FIG. 2, the probe housing 102 houses at its distal end 106 (see FIG. 1) one or more light sources 214 (which are LEDs in some embodiments, as discussed above with regard to FIGS. 1A and 1B), a camera 216 (which may be a high-resolution digital camera or imaging sensor(s)), an ultrasonic sensor 218, and one or more other sensors 220, which are all operably connected to the electronic circuit 208. In some embodiments, the electronic circuit 208 operably connects the CIS processor 202 to the components 214, 216, 218 and 220 (the camera, light source(s), ranging sensor and other sensors) and operates to buffer signals between those components and the CIS processor 202 during use of the CIS device 100. As explained above, in some implementations the light source 214 comprises a plurality of light-emitting diodes (LEDs) which are controllable by the CIS processor 202, for example, to emit bright white light, blue light and green light, which illuminance may occur at different light intensities and in different LED combinations to obtain a particular probe procedure image or images. In addition, the storage device 210 (or memory) stores processor executable instructions which when executed cause the CIS processor 202 to operate as disclosed herein.

As shown in FIG. 2, the cervical imaging system 200 also includes a host system 222 operably connected to a display 224. The host system 222 may be a personal computer, tablet computer, a smartphone (either an Android™ device or an iPhone) or other type of digital device operable by medical personnel or other person in combination with the CIS device 100. In some embodiments, the host system 222 is operably connected to a display 224 that may be a touch-screen, and to a database 226 that may be any type of data storage device. The database 226 may be configured for storing data and instructions (including various application programs) which when executed cause the host system 222 to communicate and/or operate with the CIS device 100 as disclosed herein. In addition, the database may store at least one of current image data of the patient, previous image data of the patient, and any prior diagnostic data of the patient.

In some embodiments, the CIS device 100 is configured to engage in two-way communication via the communication device 211 with the host system 222, wherein the host system may be running a CIS application or CIS program. Thus, the communication device 211 may include one or more communication ports (not shown) configured for wired and/or wireless connectivity to the host system 222. For example, the communication device 211 may be a wireless communication device (not shown) that could be operably coupled to one or more antennas (not shown) and support two-way wireless communication between the processor 202 of the CIS device 100 and the host system 222 and/or other external devices (not shown). Such a wireless communication device can include, for example, one or more of a Wi-Fi modem for communicating at short range with external devices (such as the host system 222 in some implementations), and/or a local wireless network router (not shown), and/or a Bluetooth communication device for communicating at short range with Bluetooth-equipped devices, and/or a cellular modem for communicating at long range with a mobile communication network (not shown).

It is contemplated that, in some embodiments the CIS device 100 optionally includes one or more input/output devices 230 operably connected to the CIS processor 202 which may be housed within the control housing 104. Examples of the input/output devices 230 may include, but are not limited to, a touch screen (e.g., capable of not only displaying images and/or information but for also capturing finger tap inputs, finger gesture inputs, multi-finger tap inputs, multi-finger gesture inputs, or keystroke inputs from a virtual keyboard or keypad), and/or a display screen, and/or a microphone (e.g., capable of capturing voice input) and/or a speaker. In some implementations, some input/output devices 230 can serve more than one input/output function, for example, a touch screen may be operable as an input and/or output device.

In embodiments that include the input/output devices 230, the CIS processor may be operable to run a CIS application or CIS program and then to provide imaging data (such as images of the cervix) and diagnostic data (such as reconstructed image data that includes at least one region or interest (ROI), which will be explained in detail below) to the input/output device, for example, to display to a user of the CIS device 100. Accordingly, in some implementations the CIS device 100 is operable to obtain cervix image data and ranging data, process the cervix image data to remove or minimize glare, process the ranging data to obtain information concerning the location of one or more lesions and/or then segment the cervix image data into at least one region of interest (ROI). The CIS processor may also then be operable to provide one or more images of the cervix and/or information concerning the size and extent of any lesions that are found in at least one ROI to the input/output device 230 for viewing and/or use by a user of the CIS device 100. Thus, the user of the CIS device 100, who may be a doctor or other medical professional, can utilize the imaging and ranging capabilities of the CIS device to receive imaging information and/or ROI information at the point of care (POC) location via the input/output device 230 during an examination of the cervix a patient. Such information can be utilized to diagnose the patient and/or to formulate subsequent diagnostic or medical intervention plan for the patient.

As mentioned earlier, the probe housing 102 of the CIS device 100 is shaped and sized to come close to and/or contact the tissue of the cervix during an examination, and in conjunction with the one or more light sources 214, a camera 216, an ultrasonic sensor 218, and one or more other sensors 220 subject the cervix tissue to a plurality of different stimuli, for example, white light, blue light, green light and infrared and/or ultrasound stimuli. Thus, the probe housing 102 and components 214, 216, 281 and 220 are inserted through a patient's vagina to gather images and data of the surface of the cervix, including location data of areas of interest.

FIG. 3A is an example image 300 of a healthy cervix for use in contrasting with abnormal surface lesions that will be discussed below. The line 302 delineates the difference between squamous cells 304 and columnar cells 306 found in the cervix.

FIGS. 3B and 3C depict two images 310, 312 of the cervix of a patient before application of acetic acid 310 and after application of acetic acid 312, to illustrate how using acetic acid can highlight potential precancerous lesions. Specifically, it is known that acetic acid causes reversible coagulation and precipitation of proteins in the epithelial cells of the cervix and draws water out of the cells causing the cell membrane to collapse around any large abnormal nucleus (if one exists). Because of these changes, the epithelium, which is normally a transparent filter, becomes opaque and does not allow light to pass through it. As a result, reflected light from the opaque epithelium gives off a white color. In normal squamous epithelium, the cells have very low protein levels, because the cytoplasm is replaced by glycogen and the nuclei are very small or absent, and thus acetic acid does not have any effect because there is no protein to coagulate. However, in neoplastic epithelium there are many cells with a high protein content because of large nuclei, extra chromatin, and intact cytoplasm. Thus, when acetic acid is applied the excess protein gets coagulated with acetic acid and acts as an opaque barrier to light, and the reflected light gives off a white appearance. The higher the grade of neoplasia, the greater the protein content and the greater is the density of aceto-whitening.

As mentioned above, FIG. 3B is an image of the cervix 310 before applying acetic acid, whereas FIG. 3C is an image of the same cervix 312 after applying acetic acid. In this case, after application of acetic acid to the cervix the image 312 of FIG. 3C shows a lesion within the line 314 which medical personnel may interpret as likely being a precancerous lesion.

Other types of procedures can also be used to pre-treat the cervix before conducting a colposcopy to make any lesions and/or other abnormalities apparent in an image. For example, Lugol's iodine could be used, which is a solution that stains normal epithelium dark brown. Thus, Lugol's iodine is useful for delineating normal from abnormal epithelium, for defining the borders of a lesion, and for finding vaginal lesions. It should also be noted that squamous epithelium contains glycogen, whereas precancerous lesions and invasive cancer contain little or no glycogen. Thus, since Iodine is glycophilic upon application of Iodine the squamous epithelium will take it up and be stained dark brown or black. Thus, such procedures can be utilized to highlight and/or expose precancerous or cancerous conditions in the images taken inside the cervix by the CIS device 100.

Referring again to FIG. 2, in some embodiments the CIS device 100 may be controlled and/or be controllable by the CIS processor 202, for example to adjust the focus of the camera 216, adjust the lighting intensity of the light source (such as a plurality of LEDs) 214, and utilize the ultrasonic or ranging sensor 218 to determine a distance of the distal end 106 of the probe housing from the cervix. In addition, as mentioned above the CIS processor 202 may be operable to selectively turn ON one or more combinations of LEDs that comprise the light source 214, and/or control the taking of several images of the cervix under different combinations of lighting conditions, and/or to process received image data from the camera and remove or minimize reflections and/or other artifacts in the image(s). The CIS processor 202 may also be configured to extract standardized images of the cervix from the storage device 210 for comparison to possible abnormalities found during processing of the image data and/or for use in detecting the presence, location, and extent of lesions on the cervix. The location of any identified lesion(s) can be used by medical personnel for further investigation, such as via a biopsy, of a select portion of the cervix. Such operation is contrast with a "four-quadrant" biopsy that is currently conventionally prescribed by some doctors.

In some embodiments, the CIS processor 202 may process data received from the components of the probe (i.e., the camera 216, ultrasonic sensor 218 and/or other sensors 220) alone or in any combination and then categorize any lesion(s) that are identified from one or more images taken of the cervix. In some implementations, the CIS processor 202 of the CIS device 100 compares the categorization of the lesion found in the probed cervix with a catalogue of expected or known lesion types, which may be stored in the storage device 210, to identify the location and the extent of any such lesion(s) (how widespread the lesion(s) is or are). In embodiments disclosed herein, the storage device 210 of the CIS device stores processor executable instructions which when executed causes the CIS processor 202 via the communication device 211 to transmit the determined tissue type to a host system 222.

Thus, in some embodiments, the CIS device 100 may also be configured to determine the progression of the disease and its classification (for example, as falling within one of the CIN1-CIN3 classifications) and provide this information to a host system 222 of a physician, for example, in real-time. For example, the CIS processor 202 may determine that an identified lesion is similar to a CIN2 precancerous lesion and transmit an image of the cervix and an indication of that lesion type or designation via the communication device 211 to the host system 222, which may be a tablet computer being used by medical personnel. The tablet computer then displays the image of the cervix and indication of any abnormality on the display 224 for consideration by the physician (or other medical personnel).

In another example embodiment, the CIS processor 202 may instead obtain image and ranging data via the electronic circuit 208 from the camera 216 and ultrasonic sensor 218 and then transmit the image and ranging data via the communication device 211 to the host system 222. The ranging data is used to determine a measure of the distance the cervix is from the imaging sensor, and the distance along with the view angle of the camera is then used to determine the size of the lesion. This size of the lesion in then utilized to classify the lesion as one of CIN-1, CIN-2, CIN-3 or CIS. Next, the image of the cervix may be displayed on a display screen 216 (such as a touchscreen of a physician's smartphone) along with an indication of the lesion designation (for example, CIN-2) for consideration, for example, by a medical professional.

In some implementations, the CIS application running in the CIS device 100 communicates wirelessly with the host system 222, which advantageously allows a physician to position the camera 216 or monitor the procedure at a convenient location unhindered by connecting cables and/or an external power supply. In some embodiments, the camera 216 of the CIS device 100 under processor control is programmed to capture four to six images, each taken with different sets of LEDs activated at a time. Although the acquired image data may contain relevant information concerning an abnormality in the cervix, it may also include features obstructed by specular reflections which may affect the accuracy of a classification algorithm. For example, a camera flash may be reflected on the cervix and found in the image data. Therefore, in some implementations a glare removal algorithm is used to preprocess the image data by removing specular reflection before the CIS device 100 or the host system 222 classifies and/or determines the progression of the disease.

Color images and the correct representation of features are essential when working with medical images. The most common representation of color in images is the RGB color space, wherein RGB stands for the three primary colors: red, green, and blue. Images represented in this color space are formed by combining arrays containing values of these individual color components. For most digital images, every possible color can be formed with values in the range of [0, 255] for each primary color component, in the form:

$$C_i = (R_i, G_i, B_i)$$

where $0 \leq R_i, G_i, B_i \leq 255$

Most of the research concerning cervix image analysis focuses on converting these images to other color spaces to obtain meaningful information. Two standards are the HSV and CIELAB standards, wherein HSV stands for hue, saturation, and value, respectively. The HSV color space is commonly shown as an upside-down pyramid, wherein a vertical axis represents the V component, which stands for value, or brightness. The darkest value is at the tip of the pyramid, while the white point is at the top. The horizontal distance is the S component, or color saturation, and an angle H indicates the hue (H). This color space is used to resemble the way humans perceive color by decoupling the chromatic signals (H and S) from the brightness signal (V). Hue defines the pure color in an image, in a range of [0, 360] degrees (for example, red can be represented both by 0 and 360). Saturation describes how much white light a color contains in a range of 0 to 1, where saturation value of 1 indicates that the color is pure, while a value closer to 0 indicates more light diluting the color. Finally, a pixel's brightness is obtained by calculating the mean of the minimum and maximum value of its three color channels:

$$V = \frac{\max(R, G, B) + \min(R, G, B)}{2}$$

Color systems that describe colors in a measurable, device-independent fashion are called calorimetric or calibrated. CIELAB color space is an example of a colorimetric color space. This color model was developed with the intention to linearize the representation with respect to human color perception and to generate a more intuitive color space. Color is expressed as three dimensions: L* which represents luminosity in the range of [0, 100], where 0 is black, and 100 is white; and a* and b*, which are the components that specify hue and saturation along a green-red and blue-yellow axis, respectively. While the L* values are positive and in the range of [0, 100], values for a* and b* are usually in the range of [−127, 127] (signed 8-bit integer), but can sometimes be computed in the range of [−100, 100].

Converting cervical images into a different color space, such as HSV and CIELAB, allow for different physical representation of colors and features. This makes certain calculations and analysis more convenient. Thus, cervix regions can be segmented and the types of lesions classified based on extracting relevant information and features from selected images.

Image segmentation is a critical step when processing images for classification. Through this process, an image can be split into a given number of regions. The K-means algorithm is a type of unsupervised clustering algorithm commonly used for image segmentation due to its simplicity and speed. It divides a dataset (in this case, an image) into K classes, such that similar regions or patterns are clustered together. The objective is to find the center of each cluster $C_i$ to represent each cluster. The center of each cluster is the mean of the data points which belong to it. A distance measurement, $D(x, y) = \|x - y\|^2$, is used to determine which cluster a data point belongs to. The algorithm includes the following elements:

1. For a given number of K, the data points are randomly grouped into each cluster.
2. The center of each cluster is calculated.
3. The distance from each point to each cluster center is calculated.
4. Each point is reassigned to the nearest cluster.
5. Steps 2-4 are repeated iteratively until there are no changes in the grouping.

An example of the implementation of this algorithm to cervical region segmentation is based on converting the cervix images into HSV color space and assigning three cluster centers: the cervical region, the extra cervical region, and the endoscopic region. The input to the k-means algorithm is a pixel $P = \{p_{i,j}\}_{i=1, \ j=1}^{N,M}$, where N, M are the number of rows and columns, respectively, and $p_i = (h_i, s_i, v_i)$ is the pixel in HSV color space. $\{\hat{p}_j\}_{j=1}^{K}$ and $\hat{p}_j = (h_j, s_j, v_j)$ are the pixels to be clustered for each image. The objective is to obtain the minimum Euclidean distance between the calculated pixel points and the cluster center. Once the clustering process is completed, an area filtering can be performed to remove noise and small objects.

Another way to perform image segmentation is by using morphological filters. With these filters, it is possible to alter local structures in a binary image through a "shrinking" or "growing" process which is especially useful to remove small unwanted areas in an image without significantly altering its structure. The general way to accomplish this is as follows:

1. All structures in the image are iteratively "shrunk" by peeling off a layer of a certain thickness around the boundaries.
2. Shrinking removes the smaller structures step by step, and only the larger structures remain.
3. The remaining structures are then grown back by the same amount.
4. Eventually the larger regions should have returned to approximately their original shapes, while the smaller regions have disappeared from the image The basic morphological operations are erosion ("shrinking") and dilation ("growing") and can be implemented individually or in conjunction to perform more complex tasks. These operations go beyond removing or adding a layer of border pixels, and morphological filters require a structuring element to perform the required task. A structuring element is a small binary matrix or image which gets shifted around a picture to create the new, filtered, image.

Dilation is the morphological operation that corresponds to the concept of "growing" as mentioned above. It is defined as the following set operation:

$$I \oplus H = \{(p+q) \mid \forall p \in I, \ q \in H\}$$

where I is the binary image, H is the structuring element, and p and q are coordinate pairs (u, v) of all foreground pixels (those pixels with value of 1) in I and H, respectively. The result of this operation is a point set that is the (vector) sum of all possible pairs of coordinate points from the original sets I and H.

Erosion, on the other hand, could be interpreted as de opposite operation. It is defined as:

$$I \ominus H = \{p \in \mathbb{Z}^2 \mid (p+q) \in I, \forall q \in H\}$$

This operation can be interpreted as follows: A position p is contained in the result $I \ominus H$ if (and only if) the structuring element H—when placed at this position p—is fully contained in the foreground pixels of the original image.

Designing a morphological filter is complicated and includes selecting the appropriate structuring element which depends on the desired application. Structuring elements of quasi-circular shape, such as a disk, diamond, or octagon, are commonly used, and other common shapes are the square and rectangle.

The dilation and erosion operations can be combined into more complex operations, which are often used in practical applications, especially with medical image segmentation. These are the "opening" and "closing" operations. A binary opening is defined as $I \circ H = (I \ominus H) \oplus H$, where an erosion occurs followed by dilation, using the same structuring element. The effect of this is that all foreground structures that are smaller than the structuring element are removed. Then, the remaining structures are smoothed by the ensuing dilation and grown back to approximately their original size.

Reversing the order of these operations results in closing, defined as $I \bullet H = (I \oplus H) \ominus H$. Through this operation, holes and fissures in the foreground are eliminated, while initial region sizes remain approximately the same.

For example, an image of the cervix can be converted to CIE LAB color space and then the L component (brightness) extracted. Next, a k-means algorithm may be implemented to obtain a preliminary segmentation. Different morphological filtering operations may then be performed to remove unnecessary artifacts, such as the speculum (if used) and its reflections. In some cases the structural element may be a disk with different diameter values.

It is worth noting that, while this method shows that k-means segmentation and morphological filtering can be successful in obtaining the region of interest (ROI) in a cervical image, in some cases the process may be hand-tuned and relies heavily on the image quality and the selection of appropriate structural elements. Thus, traditional segmentation techniques can be used to preprocess cervical images, or to aid the physician performing the colposcopy in a clinical setting. However, correct lesion diagnosis ultimately depends upon the colposcopist's ability to obtain high quality images, and even then expert knowledge from a specialist is required. Following below is an explanation of deep learning techniques, which have been used by many researchers with the purpose of improving automatic image-based diagnosis.

Deep learning techniques for medical imaging applications in various disciplines, including pathological image classification, have been increasingly studied recently. Thus, research has increased concerning the use of The Convolutional Neural Network (CNN) as a tool to perform image classification with high accuracy. Like a standard neural network, a CNN is mainly built with an input layer, hidden layers, and an output layer. However, the hidden layers contain convolutional layers, ReLU (Rectified Linear Unit) activation layers, pooling layers, and a fully connected layer. These layers extract features from the input images while the network is being trained.

R-CNN, which is short for "Region-based Convolutional Neural Network", has been used to address the problem of object detection. R-CNN works by extracting regions of interest in an image that may contain an object and then computing CNN features to perform classification. In some implementations, the CNN used is AlexNet, which then extracts a feature vector for each region that is used as the input to a linear SVM classifier.

Later, Fast R-CNN and Faster R-CNN were developed to address some issues with the original R-CNN. Fast R-CNN tackles the speed issue by changing the order of extracting the region proposals and computing CNN features. Faster R-CNN aims to simplify the training process by inserting a region proposal network based on the convolutional feature map and generating the region proposals based on that. Faster R-CNN has become very important in object detection due to its ability to not only find an object in an image, but to detect the exact location of this object. This is especially useful in medical applications where segmentation is an essential step in classifying pathologies and extracting other regions of interest. Thus, the advancements in deep learning techniques have been pivotal in the development of medical imaging applications because automatic classification allows the user improve the efficiency and accuracy of clinical diagnosis by decreasing subjectivity and human bias.

Researchers have investigated the use of cervigrams (photograph of the cervix) to detect precancerous lesions on the cervix. Archived digitized cervical images from screening, taken with a fixed-focus camera, were used by for developing a method based on a deep learning algorithm for automated visual evaluation of cervical images. However, many images of the cervix show small segments of the cervical area covered by specular reflection(s). The presence of glare in cervical areas is detrimental to the image quality and assessment, since these white spots present a high brightness level and low saturation, much like the acetowhite areas that highlight precancerous lesions. This is a significant problem to solve before attempting to classify precancerous lesion degrees, and researchers have attempted to handle this issue in various ways.

The removal of specular reflections by using different algorithms that aim to recover lost information due to specular reflection have been attempted. For example, an adaptive thresholding process was used to obtain glare feature maps and remove glare, followed by a filling algorithm to estimate the color and texture in the affected areas. In another example, an automatic glare extraction and feature inpainting method was proposed that was based on obtaining and comparing luminance components from both RGB and CIE-XYZ color spaces. Although region-filling algorithms may provide an estimate of what the area would look like after removing specular reflection, such estimates may forego some texture features that can be of importance to determine the severity of a precancerous lesion. Each lesion degree has different physical characteristics besides size and color, such as punctuations and mosaics, and there have been cases of misclassification that result in over- or undertreating the affected patient.

To address specular reflection removal some algorithms were developed and tested, and the algorithm which performed best in a qualitative test was selected. Specifically, through this algorithm a brightness (perceived lightness) map is generated for each image by extracting each of the RGB channels and converting each resulting matrix from "uint8" into a "double" type variable for easier calculations, followed by normalizing the values (mapped from 0 to 255) to the range of [0 1].

It is important to note that the RGB and sRGB (standard RGB, used in computer monitors) color spaces are not linear. These non-linear values are pre-corrected with a fixed Gamma so that they can be easily visualized in a computer monitor. Therefore, it is necessary to linearize these values, referred to as R', G', B' to distinguish them from the nonlinear R, G, and B channels. The normalized RGB values are the input to the following gamma correction:

$$R' = f(R),\ G' = f(G),\ B' = f(B)$$

$$\text{with } f(c) = \begin{cases} \dfrac{c}{12.92} & \text{for } c \leq 0.0405, \\ \left(\dfrac{c + 0.055}{1.055}\right)^{2.4} & \text{for } > 0.0405 \end{cases}$$

A weighted sum of the linearized RGB components is used to find luminance (or luminous intensity). Luminance is an objective measurement of brightness, and it is calculated as follows:

$$Y = 0.2126 \cdot R' + 0.7152 \cdot G' + 0.0722 \cdot B'$$

While luminance is a measurable attribute (measured in Candela per square meter, $cd/m^2$), brightness is a "perceived", or subjective, value. It can just be scaled, rather than measured in a scale of 0-100%. Using perceived lightness to analyze images can be a more intuitive way than when using luminance. The CIE LAB color space was used to obtain perceived lightness from the calculated luminance (Y) and is calculated as follows:

$$L^* = \begin{cases} 903.3 \cdot Y & \text{for } Y \leq 0.008856 \\ 116 \cdot Y^{1/3} - 16 & \text{for } Y > 0.008856 \end{cases}$$

The algorithm discards the brightest values and averages the remaining pixels so that the resulting image is bright and preserves important features. Specifically, the algorithm successfully eliminates specular reflection while maintaining relevant features in the image, and thus an CIS device application uses the algorithm to remove glare from captured images of the cervix of a patient. In some implementations, a Convolution Neural Network (CNN) is then used to detect the presence and location of lesions, and the distance of the cervix from the distal end 106 of the probe housing can be measured using the range sensor and used to estimate the size of lesions. This information can then also be uploaded, for example, via the Internet or other network to a secure server (or to the host system 222) for further processing and/or for future processing to improve the accuracy of the CIS device system through machine learning.

In some embodiments of the CIS device system, such as that shown in FIG. 2, a desktop application or CIS intake application is utilized to capture relevant patient information, which may be limited to an ID number, demographic data, and observation notes. In some implementations, a profile with this information is generated for each patient as a digital file, which may also include both images and video of the patient captured, for example, by connecting a digital camera (not shown) to the host system 222. The patient's profile and other pertinent information can be updated with each visit, if necessary, by opening the CIS desktop application and adding the data. In some embodiments, a "View" tab appearing on the display screen of the user's device (such as a tablet computer) allows medical personnel to view the images of the cervix captured during the current session or to select images captured during one or more previous patient visits. The CIS application may also display an "Analyze" tab which can be selected by the user to either perform a glare removal process, region of interest (ROI) selection, or both. It should be noted that ROI selection is not available if the image of the cervix has not been analyzed for glare removal, as discussed below.

In some embodiments, a glare removal algorithm generates a brightness map for each image. For each pixel, the brightest values will represent the areas where specular reflection is predominant and these values are discarded and the red, blue and green (RGB) values from the other images will be averaged to form a reconstructed image. The preprocessed image will then be segmented to represent only the Region of Interest (ROI) in order to determine the location of any lesions and their size. In particular, the ROI is the area covered only by the cervix, without any of the surrounding artifacts, such as those which may be added by use of a speculum. An example of the necessary segmentation is represented on FIGS. 4A and 4B.

FIG. 4A depicts an original image 400 of the cervix of a patient which contains several areas of interest. FIG. 4B shows a manual segmentation between boundary lines 402 and 404 of the cervical region of interest (ROI) 410, wherein areas 414, 416 and 418 are recognized as specular reflection (SR) areas, and wherein area 412 can be diagnosed as being an acetowhite staining (CIN-1) area interpreted as being a pre-cancerous lesion. In some embodiments, a previously trained Convolution Neural Network (CNN) is used to detect the presence and location of any lesions. Next, the distance of the cervix from the probe is measured using the ultrasonic range sensor, and this value is used to estimate the size of any such lesion.

In some embodiments, the CIS device 100 may be operable to measure bio-impendence of tissues of the cervix and can be utilized to examine the tissues of the cervix for clinical or diagnostic purposes. For example, the CIS device may be configured to provide diagnostic and/or clinical information to further assist a diagnostician or clinician in diagnosing and/or examining pregnant and/or non-pregnant patients.

As mentioned above, in some implementations a CIS application intake program can be used to capture relevant patient information, for example an ID number, demographic data, and observation notes. For each patient, a profile can then be generated with this information, and images and video can be captured by operably connecting the camera 216 of the CIS device 100 to the host system 222 (which may be a laptop computer or smartphone). Moreover, in some embodiments the CIS processor 202 is configured to compare cervix image data with past cervix testing data of the patient to determine any progression of lesions, and is configured for communications with the host system 222 and/or the database 226 to register and/or store patient data.

As also mentioned above, the current screening method for cervical cancer is visual inspection with use of acetic acid (VIA). Acetic acid works primarily by dehydrating the cell, which leads to desiccation of its cytoplasm. Since premalignant and malignant cells have a high nuclear-to-cytoplasmic ratio, they reflect greater amounts of white light than is absorbed when acetic acid is applied. Consequently, abnormal tissue appears to stain white with acetic acid. Unfortunately, VIA shows poor diagnostic accuracy due to the inherent subjectivity of visualizing precancerous cervical lesions, the inconsistent lighting conditions in clinics and the inadequate precancerous lesion detection training typically provided in Low-Middle Income Countries (LMICs).

In some cases, prior to VIA screening, the cervix is washed with a saline solution and then observed under green light. Since hemoglobin absorbs green light, illuminating tissue with green light during a cervical exam highlights the contrast associated with atypical blood vessels and helps in visualizing vasculature. On the other hand, application of acetic acid differentially increases the light scattering of neoplastic lesions, making them easier to visualize under white light.

The use of fluorescent dyes such as fluorescein sodium during surgery to mark tumor tissue has been known for many decades. While this technique was used during surgery to remove tumor tissue from the brain, the method was not in widespread use as the background fluorescence of the normal brain tissue made it hard to differentiate tumor from normal tissue. However, advances in imaging and visualization technology makes it possible to adapt this method for screening pre-cancerous cells in the cervix.

FIG. 5 is a flowchart illustrating a CIS device process 500 according to embodiments disclosed herein. To initiate a cervical examination, a user (such as a physician) may flip an ON/OFF switch on the CIS device to illuminate 502 a light source (which may include a plurality of LEDs) either immediately before or during examination of the cervix of a patient. The CIS processor of the CIS device then receives 504 cervical image data from the camera, and in some embodiments also receives 506 ranging data from a ranging sensor. Next, the CIS processor generates 508 a reconstructed image that includes reduced specular reflections. In some implementations, generating the reconstructed image includes generating a brightness map using the received image data, discarding areas of the brightness map where specular reflection is predominant, and then averaging red, blue and green (RGB) value data (generated by LEDs) from the image data to form the reconstructed image.

Referring again to FIG. 5, the CIS processor next segments 510 the reconstructed image into at least one region of interest (ROI). Lastly, the CIS processor transmits 512 the segmented reconstructed image, which includes ROIs to a host system. In some implementations, after segmenting the reconstructed image data into at least one ROI the CIS processor also generates location data and size data of any lesions in the ROI based on the location data and may also transmit the location data and size data of any such lesions to the host system.

Thus, implementations of the CIS device and CIS system as disclosed herein are operable to process cervix image data to remove or minimize glare, to segment the cervix image data into at least one region of interest (ROI) and to provide information concerning the size and extent of any lesions that are found to a user of a host system in an efficient and cost-effective manner.

The CIS device 100 disclosed herein beneficially enables up-close imaging of the cervix of a patient in high resolution without the need for costly and bulky equipment, such as a Colposcope. In addition, the CIS device is a low-cost, portable device that is easy to use, and thus can advantageously provide imaging and diagnostic capabilities at Point of Care (POC) locations in low-resource settings (for example, in third world nations). In implementations, during a single visit by the patient to the POC (such as a health care center) the CIS device captures images of the cervix in high resolution and is also capable of advantageously detecting the location, size and extent of lesions in the cervix. In some embodiments the CIS device advantageously leverages Artificial Intelligence (AI) and/or machine learning algorithms to aid a physician in making preliminary evaluations in the field during patient testing. Furthermore, the CIS device and the CIS system disclosed herein are capable of learning from the cervix testing data and/or screening data of patients to improve upon the accuracy of the screening process for future patient testing. Yet further, implementations of the CIS device include an algorithm which removes glare from images obtained during the testing procedure.

Moreover, it is contemplated that in some implementations, the CIS device will be used remotely by a trained colposcopist located at a remote location to assist a point of care ("POC") provider in evaluating images acquired by CIS device. In addition, a remote trained colposcopist may be able to assist the POC provider in validating any findings as well as in using the images to determine whether or not follow-up care, such as a biopsy, is advisable for the patient. Thus, the CIS device may play an important role in the developing field of telemedicine.

As used herein, the term "computer" should be understood to encompass a single computer or two or more computers in communication with each other.

As used herein, the term "processor" or "microprocessor" should be understood to encompass a single processor or microprocessor or two or more processors or microprocessors in communication with each other.

As used herein, the term "memory" should be understood to encompass a single memory or storage device or two or more memories or storage devices.

Any descriptions and/or illustrations of processes herein should not be considered to imply a fixed order for performing process steps. Rather, the process steps may be performed in any order that is practicable, including simultaneous performance of at least some steps and/or omission of steps.

Although the present disclosure has been described in connection with specific example embodiments, it should be understood that various changes, substitutions, and alterations apparent to those skilled in the art can be made to the disclosed embodiments without departing from the spirit and scope of the disclosure.

What is claimed is:

1. A method for automatic, image-based detection of abnormalities in a patient's cervix comprising:
   illuminating, by a processor, a light source affixed to a distal end of a probe housing;
   receiving, by the processor, cervical image of the patient from a camera affixed to the distal end of the probe housing, wherein the cervical image comprises cervical image data;
   receiving, by the processor, ranging data from a ranging sensor affixed to the distal end of the probe housing;
   generating, by the processor based on the cervical image data, a reconstructed image having reduced specular reflections, wherein the generating a reconstructed image comprises:
   generating a brightness map using the cervical image data, wherein the generating a brightness map comprises:
   converting cervical image data to a CIELAB color space, wherein the CIELAB color space comprises hue values, a saturation values, and a luminosity values, wherein the luminosity values are in the range of 0 to 100 where 0 is black and 100 is white;
   generating a structuring element, wherein the structuring element comprises a binary matrix or a binary image, and wherein the structuring element can be added to the cervical image data to make a filtered image;
   performing erosion on the cervical image, wherein the performing erosion comprises:

removing any foreground structures that are smaller than the structuring element, wherein the removing any foreground structures comprises:

adding the structuring element to the cervical image data at one or more positions of the cervical image; and deleting any foreground pixels of a cervical image of the cervical image data that are not fully contained by the structuring element;

performing dilation on the cervical image, wherein the performing dilation comprises:

generating a point set, wherein the generating a point set comprises a vector sum of one or more pairs of coordinate points from the cervical image data and the structuring element, wherein the coordinate points comprise foreground pixels and background pixels, and wherein the coordinate pairs of all foreground pixels have a value of 1; and discarding areas of the cervical image where a specular reflection is predominant to make a brightness map, wherein the discarding areas of the cervical image comprises performing erosion on the cervical image followed by performing dilation using the same structuring element to remove one or more foreground structures that are smaller than the structuring element and the remaining structures are smoothed by the ensuing dilation; and normalizing the luminosity values of the brightness map to make the reconstructed image;

segmenting, by the processor, the reconstructed image into at least one region of interest (ROI) of the cervix;

identifying, by the processor, a lesion in the ROI of the cervix;

determining, by the processor based on the ranging data, a distance of the cervix from the camera and a view angle of the camera; and generating, by the processor based on the distance of the cervix from the camera, a size of the lesion.

2. The method of claim 1, wherein the transmitting of the reconstructed image comprising the at least one ROI and the location and size data of the lesion is to the host system operably connected to a database configured for storing data and instructions.

3. The method of claim 2, further comprising:

comparing, by the host system, the reconstructed image comprising the at least one ROI with previous image data of the patient to determine any changes in the cervix of the patient.

4. The method of claim 1, further comprising, subsequent to segmenting the reconstructed image into the at least one ROI:

comparing, by the processor, the at least one ROI to known abnormal tissue type data stored in a storage device;

identifying, by the processor based on the comparison, a lesion type; and wirelessly transmitting, by the processor, an indication of the lesion type to the at least one of a host system and an input/output device.

5. The method of claim 4, wherein the indication of the lesion type comprises one of normal tissue, pre-cancerous tissue or cancerous tissue.

6. The method of claim 1, further comprising:

wirelessly transmitting, by the processor, the segmented preprocessed image data for each cervical image to the at least one of a host system and an input/output device.

7. The method for automatic, image-based detection of abnormalities in a patient's cervix of claim 1, wherein the structuring element has a shape selected from the group consisting of: a disk, diamond, square, rectangular, and octagon.

8. The method for automatic, image-based detection of abnormalities in a patient's cervix of claim 1, wherein the performing dilation on the cervical image comprises a set operation represented by a formula, $I \oplus H = \{(p+q) | \forall p \in I, q \in H\}$, wherein I is the binary image, H is the structuring element, and p and q are coordinate pairs of one or more foreground pixels in I and H, respectively.

9. A portable cervical imaging device for capturing cervical images of a patient comprising:

a probe housing comprising a camera, a ranging sensor, and input/output device and a light source; and a control housing connected to the probe housing, the control housing comprising a CIS processor, a communication device, a power supply and a storage device, wherein the storage device stores processor executable instructions which when executed causes the processor to:

illuminate the light source;

receive from the camera cervical image data of the patient, wherein the cervical image data comprises Red Green Blue (RGB) color space with values in the range from 0 to 255 for each color;

receive ranging data from the ranging sensor;

generate a reconstructed image based on the cervical image data having reduced specular reflections, wherein the generating a reconstructed image comprises:

generating a brightness map using the cervical image data, wherein the generating a brightness map comprises:

converting cervical image data to a CIELAB color space, wherein the CIELAB color space comprises hue values, a saturation values, and a luminosity values, wherein the luminosity values are in the range of 0 to 100 where 0 is black and 100 is white;

generating a structuring element, wherein the structuring element comprises a binary matrix or a binary image, and wherein the structuring element can be added to the cervical image data to make a filtered image;

performing erosion on the cervical image, wherein the performing erosion comprises:

removing any foreground structures that are smaller than the structuring element, wherein the removing any foreground structures comprises:

adding the structuring element to the cervical image data at one or more positions of the cervical image; and deleting any foreground pixels of a cervical image of the cervical image data that are not fully contained by the structuring element;

performing dilation on the cervical image, wherein the performing dilation comprises:

generating a point set, wherein the generating a point set comprises a vector sum of one or more pairs of coordinate points from the cervical image data and the structuring element, wherein the coordinate points comprise foreground pixels and background pixels, and wherein the coordinate pairs of all foreground pixels have a value of 1; and discarding areas of the cervical image where a specular reflection is predominant to make a brightness map, wherein the discarding areas of the cervical image comprises performing erosion on the cervical image followed by performing dilation using the same structuring element to remove one or more foreground structures that are smaller than the structuring element and the remaining structures are smoothed by the ensuing dilation; and normalizing the luminosity values of the brightness map to make the reconstructed image;

segment the reconstructed image into at least one region of interest (ROI) of the cervix; identify a lesion in the ROI of the cervix;

determine, based on the ranging data, a distance of the cervix from the camera and a view angle of the camera;

generate, based on the distance of the cervix from the camera, a size of the lesion.

10. The device of claim 9 wherein the light source comprises a plurality of light emitting diodes (LEDs).

11. The device of claim 10, wherein the plurality of LEDs includes at least one white LED, one blue LED, and one green LED.

12. The device of claim 9, further comprising an electronic circuit operably connected between the processor and the camera, the light source and the ranging sensor, and wherein the electronic circuit converts output signals from at least one of the camera and the ranging sensor into digital signals for input to the processor.

13. The device of claim 9, wherein the storage device further comprises, subsequent to the instructions for segmenting the reconstructed image into the at least one ROI, instructions which when executed cause the processor to:

compare the at least one ROI to known abnormal tissue type data stored in the storage device;

identify, based on the comparison, a lesion type; and wirelessly transmit an indication of the lesion type to the at least one of a host system and an input/output device.

14. The device of claim 13, wherein the indication of the lesion type comprises one of normal tissue, pre-cancerous tissue or cancerous tissue.

15. The device of claim 9, wherein the storage device stores at least one of current image data of the patient, previous image data of the patient, and any prior diagnostic data of the patient.

16. The device of claim 15, wherein the host system is operably connected to a database and wherein at least one of current image data of the patient, previous image data of the patient, and any prior diagnostic data of the patient are stored in the database.

* * * * *